United States Patent [19]
Keith et al.

[11] Patent Number: 5,609,156
[45] Date of Patent: Mar. 11, 1997

[54] FOETAL MONITOR

[75] Inventors: Robert D. F. Keith; Keith R. Greene; Emmanuel C. Ifeachor, all of Plymouth, Great Britain; Jennifer Westgate, Auckland, New Zealand

[73] Assignee: University of Plymouth, Great Britain

[21] Appl. No.: 351,294

[22] PCT Filed: Jun. 9, 1993

[86] PCT No.: PCT/GB93/01231

§ 371 Date: Jan. 24, 1995

§ 102(e) Date: Jan. 24, 1995

[87] PCT Pub. No.: WO93/25971

PCT Pub. Date: Dec. 23, 1993

[30] Foreign Application Priority Data

Jun. 9, 1992 [GB] United Kingdom .................. 9212133

[51] Int. Cl.$^6$ ................................................ A61B 5/0444
[52] U.S. Cl. .......................................... 128/670; 128/698
[58] Field of Search ......................... 364/413.02, 413.05, 364/413.06; 128/670, 700, 698, 630

[56] References Cited

U.S. PATENT DOCUMENTS 3,989,034  11/1976  Hojaiban ................................ 128/698
4,964,410  10/1990  Leahey et al. ......................... 128/696

FOREIGN PATENT DOCUMENTS 2403058  4/1979  France .
2021779  12/1979  United Kingdom .

OTHER PUBLICATIONS

Alonso et al., "Development of an Adviser System for Foetal Diagnosis During Labor," Proceedings of the Annual International Conference of the IEEE Engineering in Medicine and Biology Society, vol. 10, pp. 1355–1357.

Karakas et al., "A Neural Net Learning Algorithm for Design of Cardiotocograph Signal Evaluation Expert System: MYDEARBABY 90/2.47," Proceedings of Database and Expert Systems Application, Springer Verlag, pp. 427–431.

Karnas et al., "Expert Systems for Evaluating Fetal Monitor Signals," Proceedings of the ISCIS III, NOVA Science Publ., New York, Cesme, Turkey, pp. 317–322.

Alonso–Betanzos et al., "Foetos: An Expert System for Fetal Assessment," IEEE Transactions on Biomedical Engineering, vol. 38, pp. 199–211.

Primary Examiner—William E. Kamm
Assistant Examiner—Kennedy J. Schaetzle
Attorney, Agent, or Firm—Clifford W. Browning; Woodard, Emhardt, Naughton, Moriarty and McNett

[57] ABSTRACT

A medical signal analyzer comprises a sensing device (1) including at least one sensor for monitoring at least one parameter derived from a physiological measurement taken from a patient under observation, a data collection device (2), coupled to the sensing device for receiving and sampling an output signal of the sensing device and generating digital signals representative of the parameter over a predetermined time interval, a data analysis means (4) comprising means operable to recognize in the digital signals received over a signal link from the data collection device a plurality of predetermined information features, and means for classifying at least one of the said features, to produce first output signals representative of the existence of such features and representative of feature classifications, signal storage means (6) arranged to receive and store the said first output signal as a short term knowledge base, database storage means for storing reference data as a long term knowledge base (10), an inference engine arranged to process signals representative of the short term and long term knowledge bases automatically to produce conclusion signals, and indication means (16) coupled to receive signals produced by the inference engine to provide an indication of said conclusion signals.

14 Claims, 8 Drawing Sheets

|  CTG \ ST Waveform | Normal | High & Stable | Negative Rising |
| --- | --- | --- | --- |
| Normal | No action | No action | FBS or deliver |
| Intermediate | No action | Wait 1h FBS or Deliver | Deliver |
| Abnormal | Wait 1h FBS or Deliver | Deliver | Deliver |

FIG.13.

FOETAL MONITOR

This application is a 371 of PCT/GB93/01231, filed Jun. 9, 1993.

This invention relates to a medical signal analyzer and particularly to an analyzer for use in the monitoring and processing of medical signals representing selected physiological parameters, and as an aid to interpretation of the signals.

In a modern hospital environment, many medical instruments are available to sense and display selected physiological parameters of a patient under observation, with information frequently being plotted or displayed as a time-varying waveform. Such an instrument may additionally incorporate an alarm system which operates by crudely comparing a feature of the waveform against a preset threshold, an alarm being raised when the particular measured feature crosses the threshold. Such a prior system is prone to positive and negative false alarms; that is, raising an alarm when the patient is in no immediate danger and not raising an alarm when the patient is in danger, respectively. The false alarm rate can be sufficiently high that in practice, the alarm is frequently ignored or even disabled. The analysis of the patient's condition using a medical instrument thus relies largely on the human interpretation of a continuous waveform. Correct interpretation requires specialised training, considerable experience, skill and alertness. Since it is frequently not possible to make personnel with such experience and training available on the ward on a 24 hour basis, the usefulness of the instrument is diminished.

It is an object of the present invention to provide a medical signal analyzer which improves the processing and aids the interpretation of patient-derived, medical signals.

This is achieved according to the invention by providing a medical signal analyzer comprising a sensing device including at least one sensor for monitoring at least one parameter derived from a physiological measurement taken from a patient under observation during labour and including a sensor for monitoring uterine movements and a sensor for monitoring foetal electro-cardiogram, a data collection device, coupled to the sensing device for receiving and sampling an output signal of the sensing device and generating digital signals representative of the parameter over a predetermined time interval, a data analysis means comprising means operable to generate a reference signal from the digital signals and to recognize in the digital signals received over a signal link from the data collection device a plurality of predetermined information features by automatically analysing the digital signals in relation to the reference signal, and means for classifying at least one of the said features, to produce first output signals representative of the existence of such features and representative of feature classifications, signal storage means arranged to receive and store the said first output signal as a short term knowledge base, database storage means for storing reference data as a long term knowledge base, an inference engine arranged to process signals representative of the short term and long term knowledge bases automatically to produce conclusion signals, and indication means coupled to receive signals produced by the inference engine to provide an indication of said conclusion signals.

An inference engine can be arranged to receive and process signals representative of the short term and long term knowledge bases automatically to produce conclusion signals, and a display device coupled to receive signals produced by the inference engine displays a visual indication of the conclusion signals.

The sensing device is preferably a device that senses the uterine pressure of a pregnant woman and foetal electro-cardiogram (ECG) which can be used to derive foetal heart rate. Such a device, which usually produces a continuous time-varying, parallel trace indicating uterine pressure and foetal heart rate called a cardiotocogram (CTG), is commonly called a CTG monitor. By analysing the signal collected from the sensing device, features comprising time variation of the parameters may be recognized in the digital signals. These information features may comprise at least one of baseline heart rate, heart rate variability, heart rate acceleration (i.e. a period of increased heart rate), heart rate deceleration (i.e. a period of decreased heart rate), uterine contraction pattern and quality of the output signal of the sensing device. The information features may be classified. A heart rate acceleration for example, may be classified as present or absent, or a heart rate deceleration may be further classified by its size and its timing in relation to uterine contractions. Patient-specific data may comprise risk factor data such as the risk of meconium, intra-uterine growth retardation, and antenatal and labour problems such as placental abruption or labour-specific event data such as data from a foetal blood sample, details of drugs and anaesthesia previously administered to the patient and details of cervical dilation. The display device may be used in combination with the operator entry interface or interfaces to interactively interrogate a user to obtain the patient-specific data. The display device may also be used to elucidate the conclusion signals.

The indication of the conclusion signals preferably comprises a recommended course of action, and may be displayed on a CRT. Alternatively lights with or without audible indications may be used to indicate the severity of the situation. Using a plurality of lights, a severity level may be indicated by assigning varying levels of severity to each respective light.

The reference signal generated from the digital signals may represent a modal average of the digital signal over a predetermined time interval.

In the case where the sensing device is a CTG monitor and the digital signals represent at least uterine pressure and foetal heart rate, the reference signal may represent the baseline heart rate. Given this information a heart rate deceleration may be recognised by quantifying, for a set of the digital signals all representing a foetal heart rate lower than the baseline heart rate, several parameters. These parameters are, typically, the period of time for which the heart rate is lower than the baseline heart rate, the magnitude of the greatest deviation below the baseline heart rate, the variability of the heart rate and the area of the minimum formed between the heart rate waveform and the baseline heart rate waveform.

The present invention will now be described by way of example, with reference to the drawings in which.

Interpreting the output of medical instruments is a complex, yet vital task in modern medical work. The following is a description of an embodiment of the invention used in a labour ward.

The management of labour is a difficult task, and often involves several clinicians at various levels. Successful management of labour depends on the continuous assessment of the condition of the foetus as well as other factors, such as progress of labour, post obstetric history and the maternal condition all of which are important in decision making. The assessment of the condition of the foetus is typically based on the following:

i) Visual analysis and interpretation of the CTG. The key features of clinical interest in the CTG include baseline heart rate and variability, number and duration of dips and accelerations in the foetal heart rate the locations and peaks of contraction, so that episodes of heart rate changes can be related to these peaks.

ii) Foetal blood sampling—Certain CTG patterns suggest a possible deterioration in the foetal condition. To determine if operative delivery is necessary an assessment of the acid/base status of the foetus from a foetal blood sample (FBS) may be made. Typically, if the pH level of the foetal blood is less than a certain threshold (e.g.7.20) there is cause for concern. However, foetal blood sampling is intermittent, time consuming, often difficult and can be stressful for both mother and foetus. Frequently foetal blood sampling is performed unnecessarily and sometimes not performed where necessary. An expert clinician will keep intervention, in the form of foetal blood sampling and operative delivery, to a minimum whilst correctly identifying those foetuses who do require action in order to prevent poor outcome.

Modern technology has yet to provide the clinician with a simple and reliable tool for automatically assessing the condition of the baby during labour. Current electronic intrapartum recorders simply produce outputs of the foetal heart rate together with uterine contractions. These outputs require a great deal of experience and physiological knowledge to interpret appropriately, but this expertise is not available to all labour wards day and night, leading to incidents of unnecessary medical intervention at birth—30% of emergency caesarean sections were deemed unnecessary in a recent study—or more importantly, failure to intervene when necessary which can lead to neurological damage and mortality. Increasing anxiety about obstetric litigation has resulted in many more interventions. These problems illustrate the significant practical problems in the full interpretation of the information in a CTG. The problems are complicated further by the difficulty of maintaining a consistent and adequate level of expertise with constantly changing clinical staff.

For this to succeed, an intelligent, automatic analysis and assessment of the vast amount of information available before and during labour is required.

Figure 1:
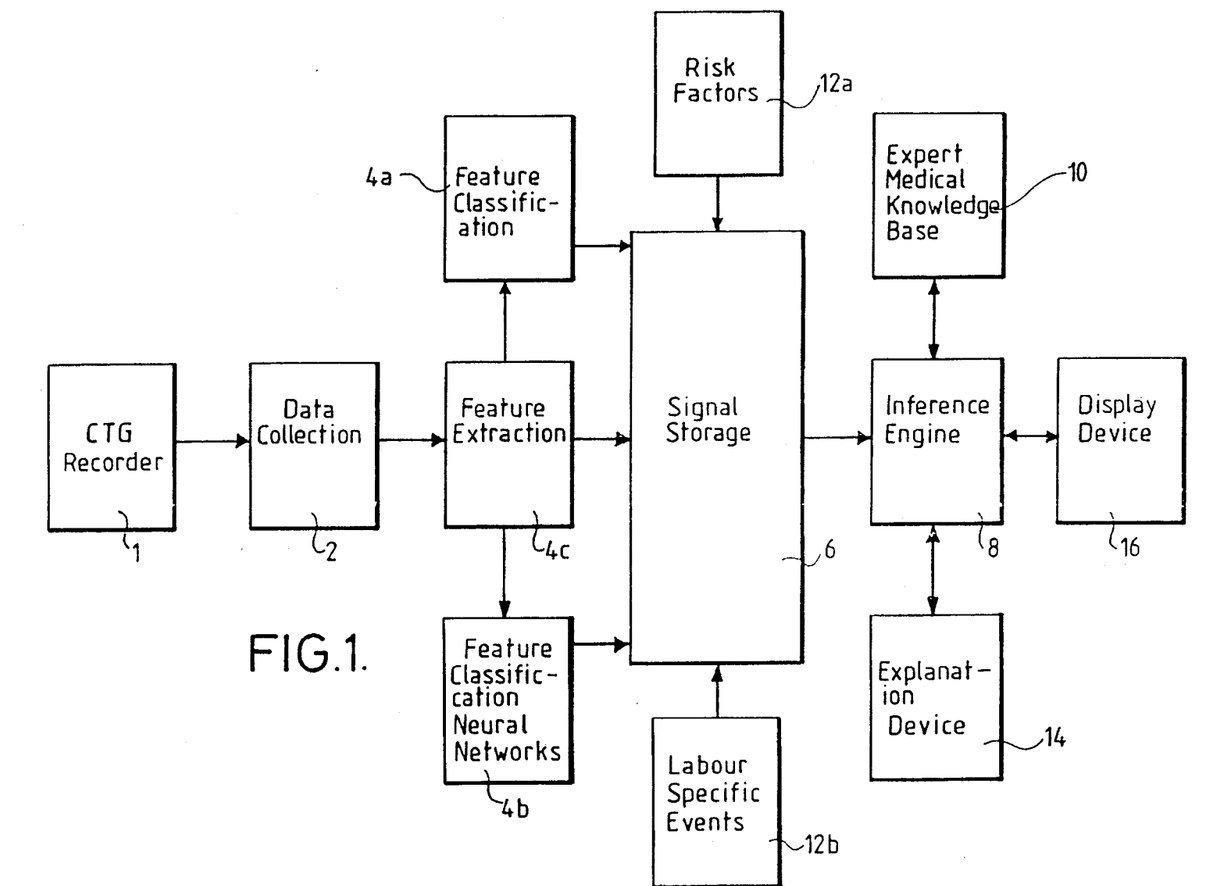
FIG. 1 is a block diagram ore medical signal analyzer in accordance with the present invention.

FIG. 1 shows a medical signal analyzer in accordance with the invention applied to this problem of analyzing and interpreting a CTG.

In a preferred embodiment of the invention, a data pre-processor (e.g. a conventional CTG recorder) is used to obtain outputs from a foetal scalp sensor and a uterine pressure sensor to obtain the foetal heart rate and uterine pressure as amplified analogue signals. These signals are digitized by a data collection device 2.

The samples are transmitted to a microprocessor-based system via a data-link.

Some of the features within the CTG which reflect foetal condition are:

1. Baseline heart rate—the heart rate about which the heart rate pattern deviates.
2. Heart rate variability—the amplitude of the high frequency perturbations about the baseline heart rate.
3. Accelerations in heart rate—relatively long term transient increases in heart rate from the baseline, classified as either present or absent.
4. Decelerations in heart rate—relative long term decreases in heart rate from the baseline, these are further classified according to their size and to their timing in relation to contractions.
5. The contraction pattern.

Another factor to be considered is the quantity of noise present in the signals.

Feature recognition and classification of the five features is performed by a data analysis device 4a, 4b, 4c as described below.

It has been found that a neural network may be used to classify decelerations in heart rate dependent on several variables. Such an approach requires an expert to train the network by example and therefore removes the need to formalize the methods. To reduce the requirement for processor power, at least some of the recognition and classification is undertaken by 'non-neural network' means which do not need training with example sets of data and which are written with initially predetermined or preset relationships pre-programmed into them.

In the embodiment described below, recognition and classification is carried out using entirely non-neural network means.

Baseline Heart rate

Figure 2:
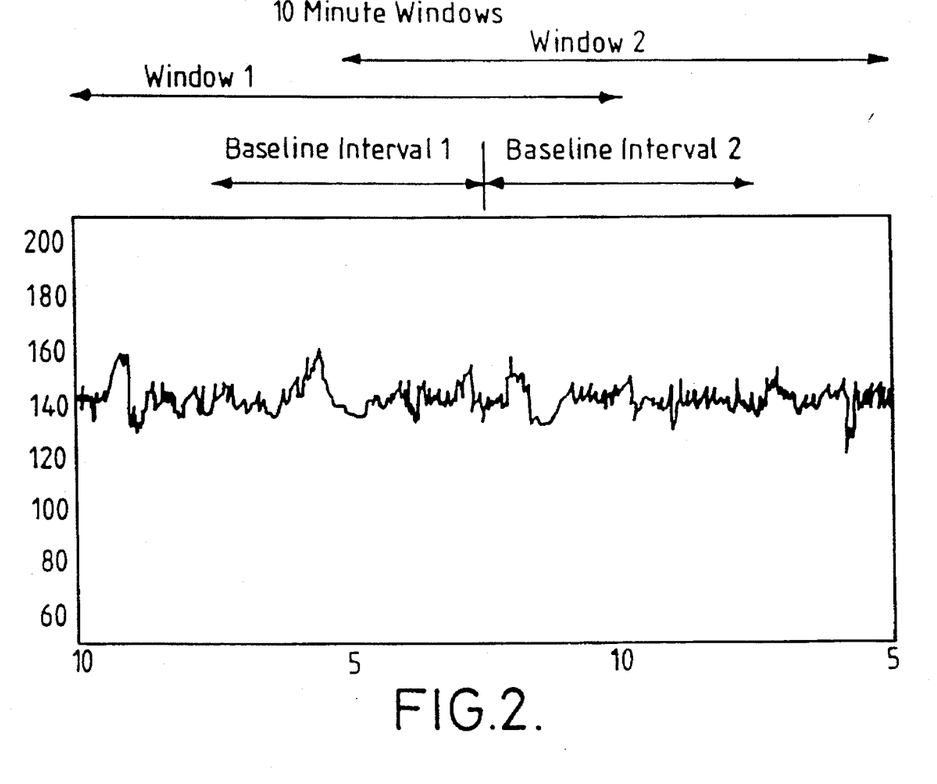
FIG. 2 shows a typical foetal heart rate trace.

The baseline foetal heart rate is assessed for a 10 minute period (or window) of heart rate recording. A typical foetal heart rate trace is shown in FIG. 2. A statistical frequency distribution is constructed for the heart rate samples within the 10 minute window. The baseline is approximately established by stepping through the heart rate range in 10 bpm windows (i.e. 1–10 bpm followed by 2–11 bpm etc.) and then finding the most densely populated or modal range of 10 bpm within the frequency distribution.

$$\text{modal range}_{j-j+10} = \max \left| \sum_{i=j}^{i=j+10} (f(x_i)) \right|_{j=0}^{j=210}$$

Where j is incremented in steps of 1 and $f(x_i)$ is the frequency of occurrence of the $x_i$ heartrate.

To save processing time, the range from 50 bpm downwards may be ignored. The modal heart rate within the above established modal range is then found and used as the value of the baseline heart rate for the interval 2.5 mins to 7.5 mins within the 10 minute window. By using a two-stage assessment of the heart rate, the effects of noise caused, for example, by disconnection of the heart rate transducer, are minimized.

After calculating the baseline heart rate for a 10 minute window, the 10 minute assessment window is incremented in time by 5 minutes. The heart rate data collected from the oldest 5 minute period are removed from the frequency distribution, and the new data added. The same process is employed to ascertain the modal range and thence the baseline heart rate for the period 2.5 mins to 7.5 mins within the new position of the 10 minute window.

This baseline heart rate value is not always adhered to. Since there is a lag of some minutes between the received signal from the transducers and the averaged output, it may be necessary to follow the signal from the transducers more closely under certain circumstances. This is the case when the heart rate falls rapidly. A baseline heart rate calculation as described above will reflect the fall, but only several minutes after the event. In this case, experience shows that urgent action should be taken and the baseline heart rate is therefore caused to track closely the input signal and to discard the averaged value under certain circumstances.

The baseline heart rate for the second interval may not be the same as for the first. This possible discontinuity is resolved by identifying the point where the trace begins to diverge from the baseline of the first interval and the point where the trace and baseline converge back again during the second. The points are identified after the first and second baseline heart rates have been calculated and the points are found by detecting a large deviation between two consecutive baseline heart rate calculations and then tracking along the data values representing the heart trace until the trace in each case is within a predetermined distance from the calculated baseline rate. The baseline within a transition region between the points is the equation of the curve joining the identified points of divergence and convergence.

Figure 3:
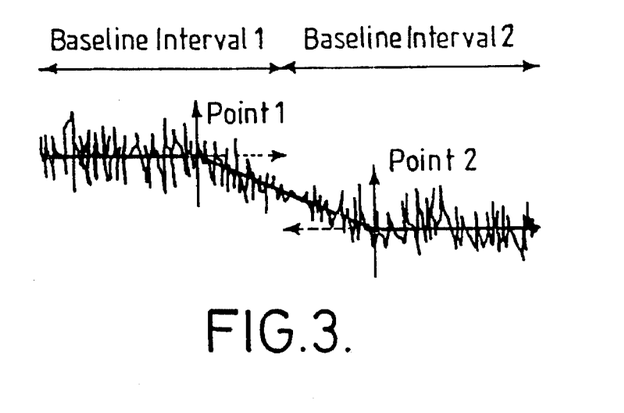
FIG. 3 shows a discontinuous heart rate baseline.

The process of dealing with a discontinuous baseline rate value is shown in FIG. 3.

After points 1 and 2 have been identified, the equation of the curve joining them is calculated which is then taken as the transitional baseline heart rate.

Heart rate variability

This refers to the maximum amplitude of irregular fluctuations assessed within epochs in the order of one minute, seen on the CTG between periodic changes such as accelerations and decelerations from the baseline heart rate. The variability can be assessed as the peak to peak variation about the local baseline, not necessarily the actual baseline heart rate, of the trace for the minute epoch. By collectively combining the interpretation from all such epochs within the section of trace under consideration, it is possible to obtain a measure of the foetal heart rate variability.

Figure 4:
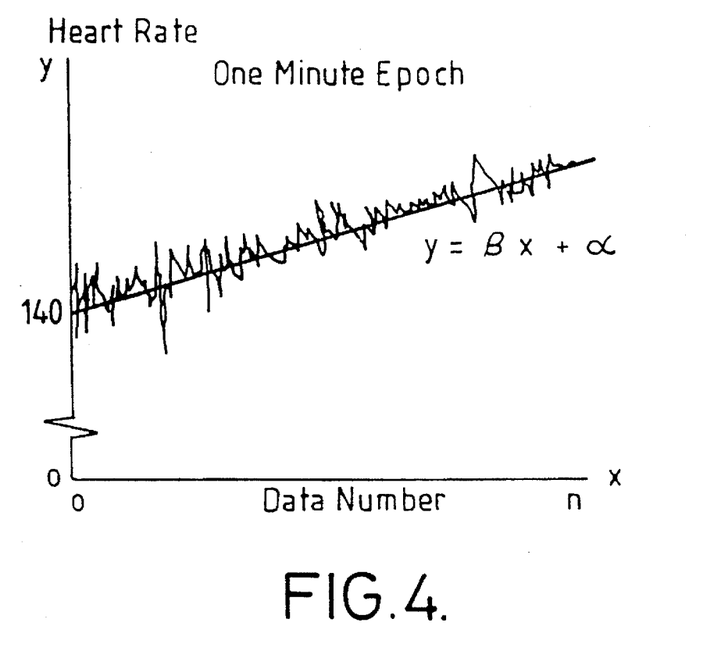
FIG. 4 shows a one minute epoch.

The analyser operates by taking a 15 minute section of heart rate recording, identifying all periodic changes (i.e. accelerations and decelerations—see below) in the heart rate section and excluding them from the analysis. A one minute assessment window is then passed over the remaining sections. The heart rate data within the window will lie on the local baseline which has the equation $$y = \beta x - \alpha$$

A one minute epoch is shown in FIG. 4.

The one minute heart rate trace will lie upon a local baseline whose equation can be found using regression analysis.

The gradient $\beta$ is calculated using regression analysis.

$$\beta = \frac{\sum_{i=1}^{n}(x_i y_i) - \frac{1}{n}\sum_{i=1}^{n}x_i \sum_{i=1}^{n}y_i}{\sum_{i=1}^{n}(x_i)^2 - \frac{1}{n}\left(\sum_{i=1}^{n}x_i\right)^2}$$

and $\alpha$ is found using $$\alpha = \bar{y} - \beta \bar{x}$$

where n is the number of heart rate samples within the one minute window and x and $x_i$ and y and $y_i$ are the abscissa and ordinate coordinates respectively (i.e time and heart rate).

Figure 5:
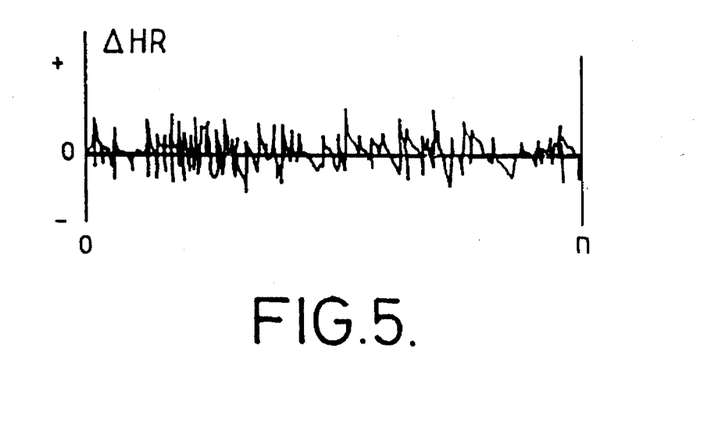
FIG. 5 shows an epoch with the baseline removed.

The equation of this line can then be subtracted from the heart rate samples to transform the data about a zero baseline thereby removing the local baseline. FIG. 5 shows an epoch processed in this way.

Figure 6:
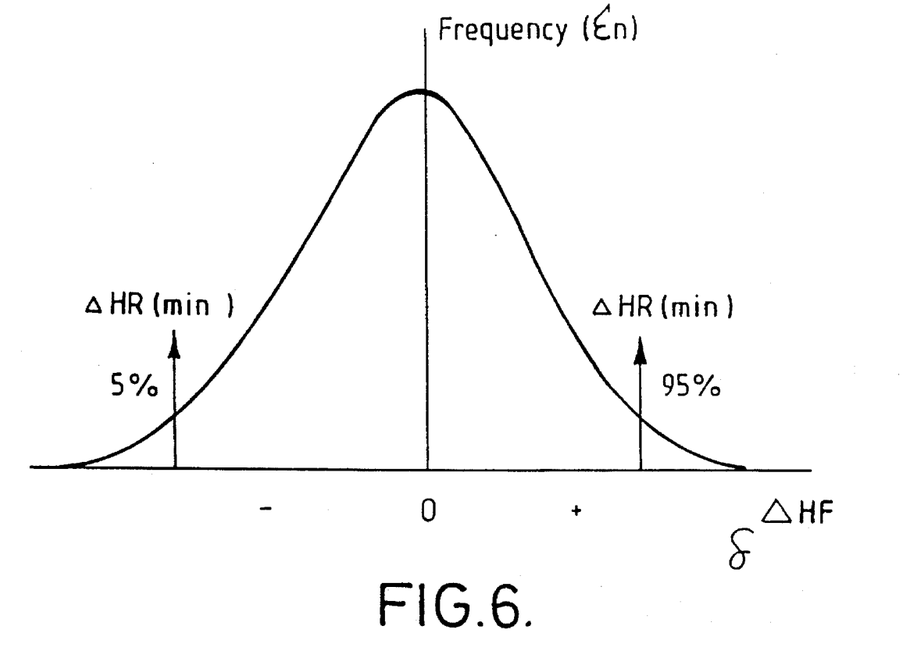
FIG. 6 shows a statistical frequency distribution of an epoch processed as shown in FIG. 5.

The statistical frequency distribution of these converted samples is then constructed and heart rate variations corresponding to the statistical 5% and 95% levels are found. The difference between these heart rates represents an assessment of heart rate variability. A representation of the frequency distribution is shown in FIG. 6.

The heart rate variability measurement is then symbolically grouped into the following classifications:

| Variability | Classification |
|---|---|
| 0–2 | Absent |
| 3–5 | Reduced |
| 6–25 | Normal |
| >25 | Increased |

Figure 7:
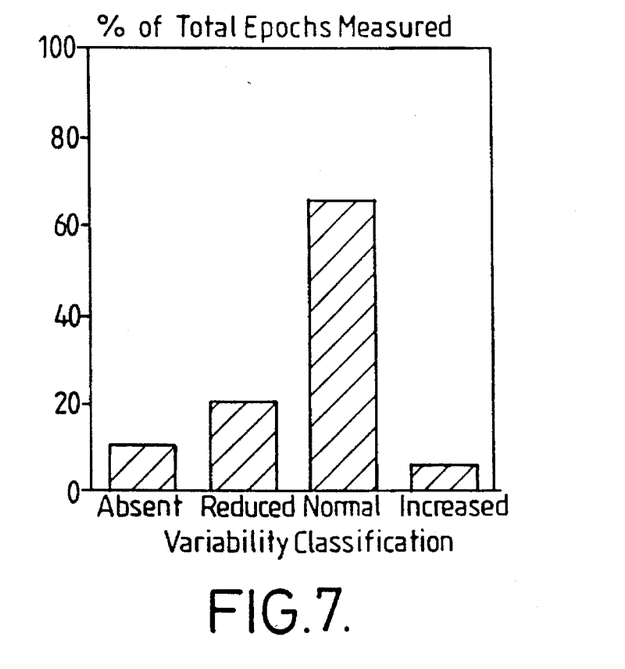
FIG. 7 shows a typical variability histogram.

This process is carried out on all one minute epochs free from accelerations and decelerations within a 15 minute period of tracing. A histogram of the results is then plotted. A typical histogram is shown in FIG. 7.

Figure 8:
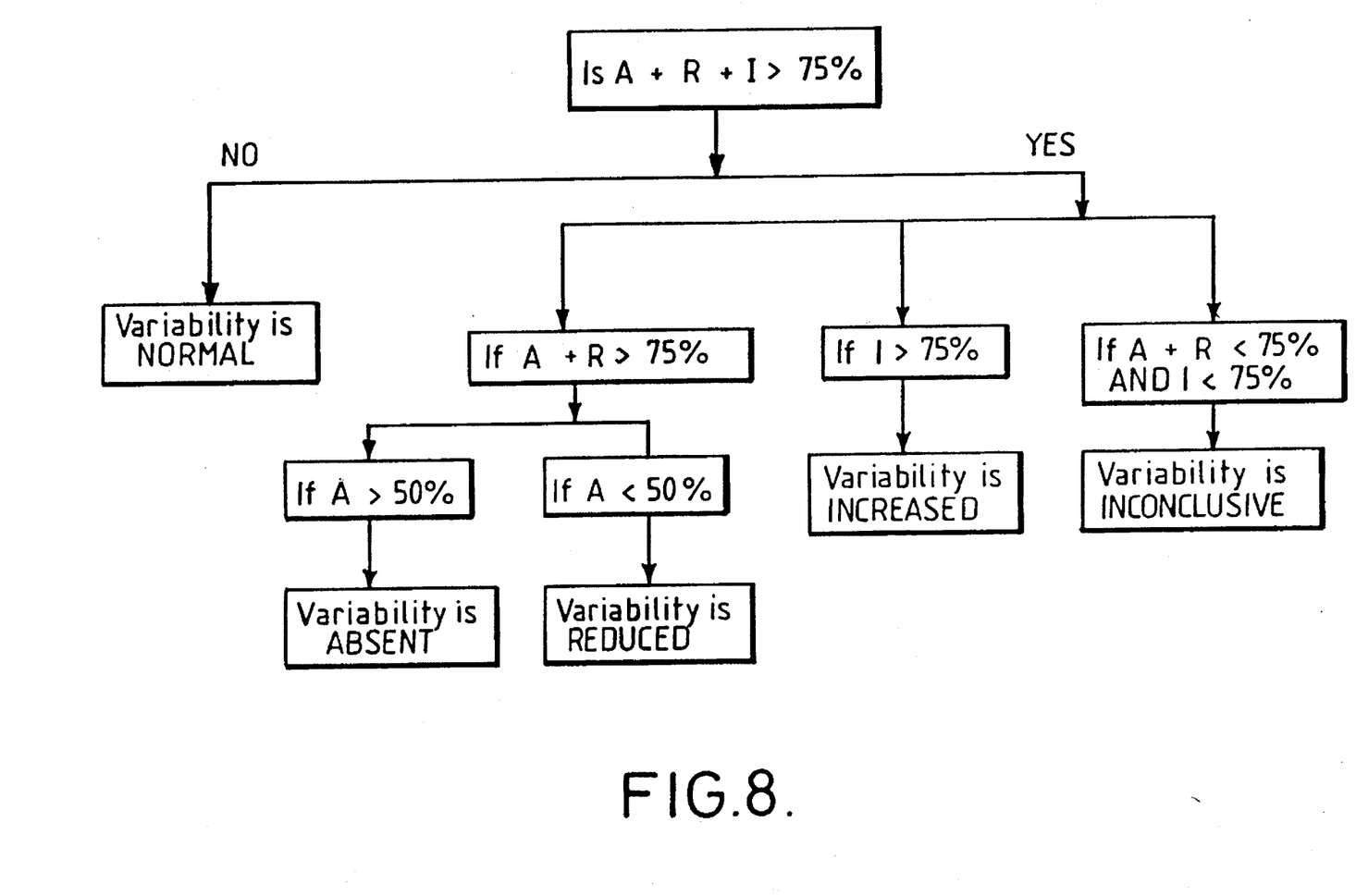
FIG. 8 shows a flow diagram for interpreting the histogram of FIG. 7.

Rules for interpreting the histogram are shown in flow diagram form in FIG. 8 (A is the number of epochs with Absent Variability, R with Reduced Variability and I with Increased Variability). An assessment of the overall heart rate variability can be obtained with the above rules.

Periodic Changes—Accelerations and Decelerations

Accelerations and decelerations are termed periodic changes. An Acceleration is a temporary increase in foetal heart rate from the basal heart rate, with a corresponding return. The complete event can last up to several minutes but is often less. These tend to be a positive indication. A deceleration is a temporary decrease in the foetal heart rate from the baseline heart rate, with a corresponding return. Decelerations can be further classified according to their timing in relation to contractions as, simultaneous or lagging (obstetrically termed early or late) as well as the severity of the deceleration, termed mild or severe. A further classification of variable decelerations depend both on shape and timing.

It is possible to define a periodic change as being a departure from the baseline of x bpm (typically x is 10–15 bpm) for a minimum period (typically greater than 15 seconds). Further classifications may be made between mild and severe using higher thresholds.

These methods were implemented but were found not to be representative of an expert clinician.

During episodes of high variability the methods identified features which were not considered as being genuine decelerations but rather the result of a highly reactive heart rate pattern. Further, during recording periods for which the variability was absent or reduced, the methods employed failed to identify features which the expert obstetrician immediately recognised as shallow decelerations. This latter point is extremely pertinent as some ominous heart rate tracings associated with the severely compromised foetus can have absent variability with shallow (a departure of 5–7 bpm) decelerations.

The criteria employed have therefore been varied from that above and the departure heart rate threshold for defining a deceleration or acceleration has been made a function of the current variability as well as the other variables normally used. A further variable, the area A, of the feature is also calculated. With this additional information, knowledge of the shape of the feature can be inferred.

Figure 9:
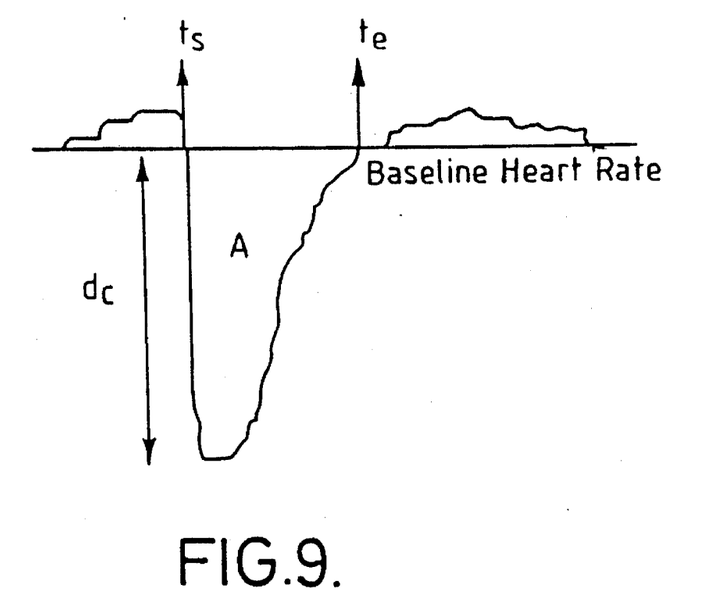
FIG. 9 shows a typical heart rate deceleration.

A typical deceleration is shown in FIG. 9. The interval $t_s$–$t_e$ is the duration of the deceleration and A is the area of the deceleration below the baseline. $d_c$ is the maximum departure from the baseline and is positive for accelerations and negative for decelerations.

Accelerations are detected when $t_e-t_s>15$ seconds, $d_c>+15$ bpm, and the area A above the baseline heart rate is greater than 112.5 square units or lost beats (bpm×time). One approach is to calculate the area of the smallest isosceles triangle that can be constructed with the thresholds indicated which has the effect of removing shapes without a sufficiently rapid rate of ascent from the baseline to the peak of the acceleration, and descent from this peak back to the baseline. Alternatively the actual area of the acceleration may be calculated using conventional techniques.

Decelerations, are detected when $t_s-t_e>15$ seconds and the departure heart rate $d_{hr}<-15$ bpm for normal variability, $<-10$ bpm for reduced variability, $<-5$ bpm for absent variability and $<-20$ bpm for increased variability.

An alternative approach to identifying decelerations is to look for a fall in the fetal heart rate below the baseline of more than 10 bpm for more than 15 seconds with an area greater than 5 lost beats. Such a deceleration may then be classified as severe if its area is greater than 20 lost beats. This algorithm may be improved by also taking account of the context of the deceleration, i.e. the surrounding variability, since this may be an indication of a poor contact for the ECG transducer apart from foetal factors which may influence variability.

As a further alternative and as mentioned above, a neural network may be used to classify decelerations. The network must be trained with a training set of sample decelerations prior to use. For complex waveforms, the number of nodes required, the need to find an exhaustive set of training examples and the time taken for the network to converge to a solution during training are prohibitive. By simplifying the inputs to the network, these overheads may be reduced to practical levels. One method of doing this involves the use of an algorithm for pre-processing the heart rate signal to identify possible decelerations and to measure the area, depth and duration of the deceleration and to measure the variability surrounding it. This information is then fed to the input nodes of the network. The network has three outputs to classify the feature as either a deceleration, not a deceleration or a severe deceleration. In this embodiment, the network therefore requires four input nodes and three output nodes. It has been found empirically that upwards of five middle nodes are required to achieve accurate and stable classification of a deceleration in this way.

Having classified a deceleration, the classification still needs considering in the light of contraction information.

Contractions

The location and magnitude of the contractions are important in categorising heart rate decelerations as well as monitoring the administration of oxytocic drugs used to control the augmentation of labour.

The analogue signal obtained from the contraction transducer and is then digitised by the monitoring equipment at a sampling frequency of 1 Hz.

Figure 10:
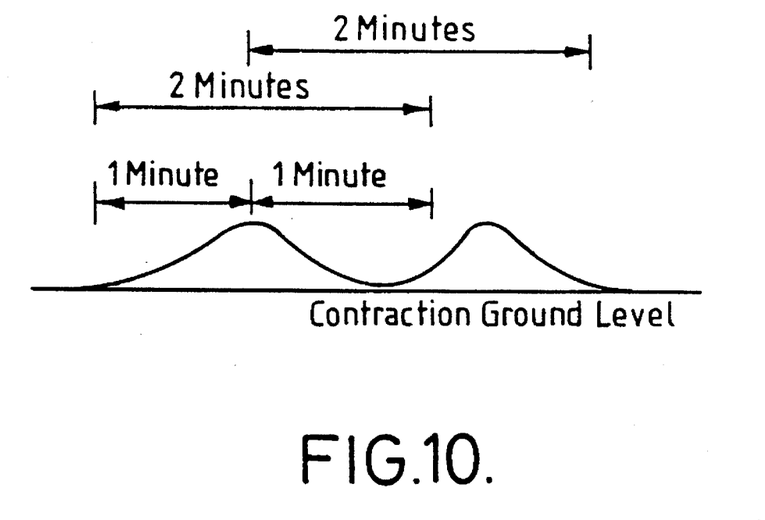
FIG. 10 shows a typical contraction waveform.

Firstly with reference to FIG. 10, a ground level from which the contraction is referenced is established.

Figure 11:
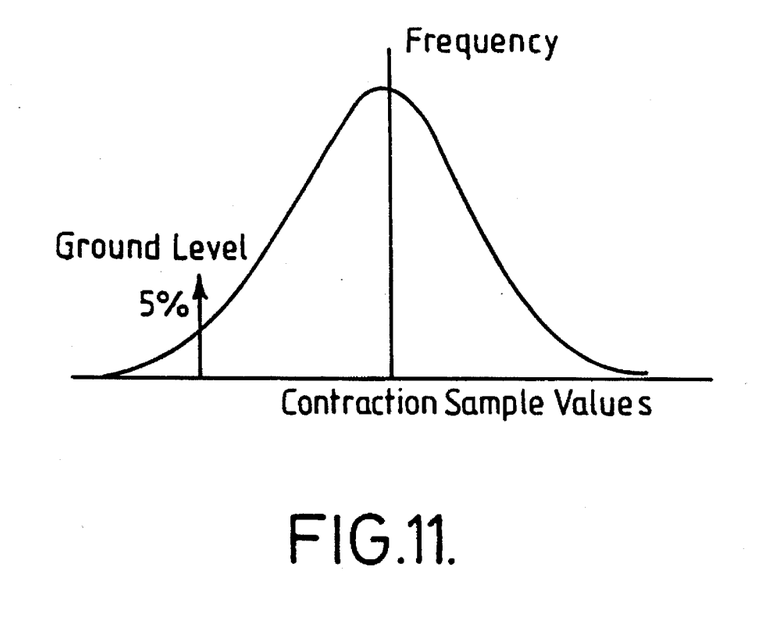
FIG. 11 shows a statistical frequency distribution of a contraction waveform.
Figure 12:
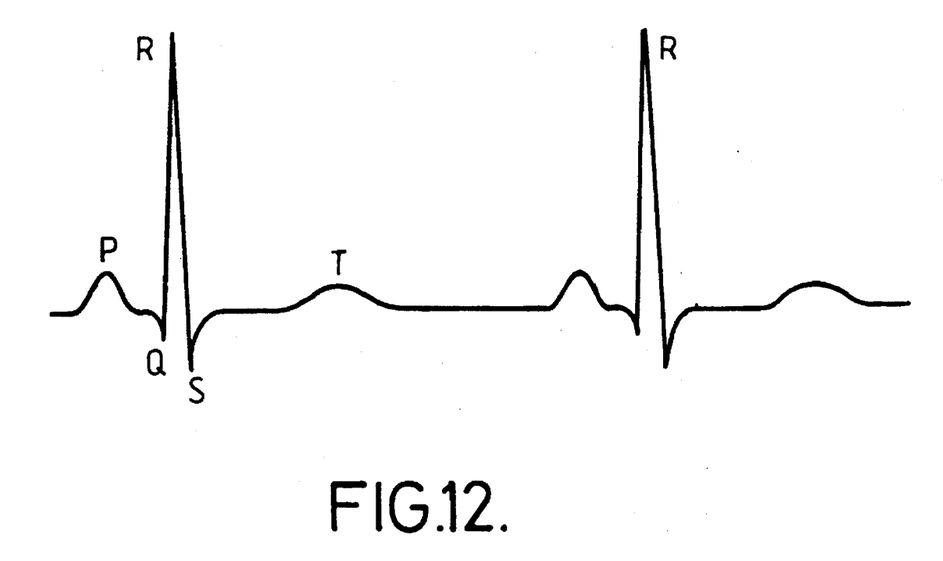
FIG. 12 shows a typical ECG trace with PQRS and T features marked.

A 2 minute window is stepped across the contraction samples with a step size of 1 minute. The frequency distribution of the samples within the 2 minute window is established. The ground level is taken to be the contraction sample value at the lower 5% cumulative frequency mark. FIG. 11 shows a statistical frequency distribution of the contraction samples within the window, with the 5% ground level marked. Taking this value rather than the minimum sample within the window reduces the effects caused by spurious noise samples. This function could be undertaken by a low-pass filter.

Once the ground level is established the contraction can be identified as a significant increase with a corresponding decrease back or near to the ground level. Hence the start, end and peak of contraction can be established. This complete episode lasts in the order of minutes which is a useful fact for discriminating between noise transients and other artifacts from genuine contractions. The level (i.e. the onset and end level) at which the increase is deemed significant is dependent on the spread or standard deviation of the frequency distribution since this is an indicator of the quality of the signal. A very narrow distribution would be indicative of a poor contact of the transducer.

The features extracted from the CTG together with information specific to the pregnancy are stored in signal storage means 6. This information represents short term knowledge pertaining to the patient, which is then processed by an expert system comprising an inference engine 8 and a database 10 which contains a long term medical knowledge base.

The medical knowledge base has been constructed using many production rules. These are obtained from knowledge elicitation exercises performed with experts. These rules provide the interpretation of the condition of the foetus based on the short term knowledge and can be used to indicate a level of concern for foetal well-being. These rules can also be used to suggest an appropriate form of action.

The inference engine applies this long term knowledge to the short-term knowledge using a forward and backward chaining strategy. The inference engine may forward chain with information previously established; for example information automatically extracted from the CTG, or information obtained interactively with the midwife (the administration of drugs, FBS results progress of the labour etc) via an operator entry interface 12a, 12b. When further information is required, the inference engine reverts to backward chaining until a goal is found. Recommendations and/or requests for further operator entry via the interface 12, are displayed on a display device 16. An explanation device 14 elucidates on information which has led to the current position in the knowledge tree.

Given the complexity of labour, foetal heart rate monitoring alone is not adequate for predicting the condition of the foetus. The addition of more variables will improve sensitivity—currently only foetal scalp blood pH is available, but at best, sampling is performed only intermittently and many medical units do not have scalp sampling facilities. The foetal ECG waveform itself can provide extra useful information. A combination of ECG variables has been shown to be more predictive of foetal acidosis than one variable alone. Further, the assessment of other information such as uterine activity, cervical dilation, progress of labour and antecedent factors is also important in deciding what course of action to take.

Figure 13:
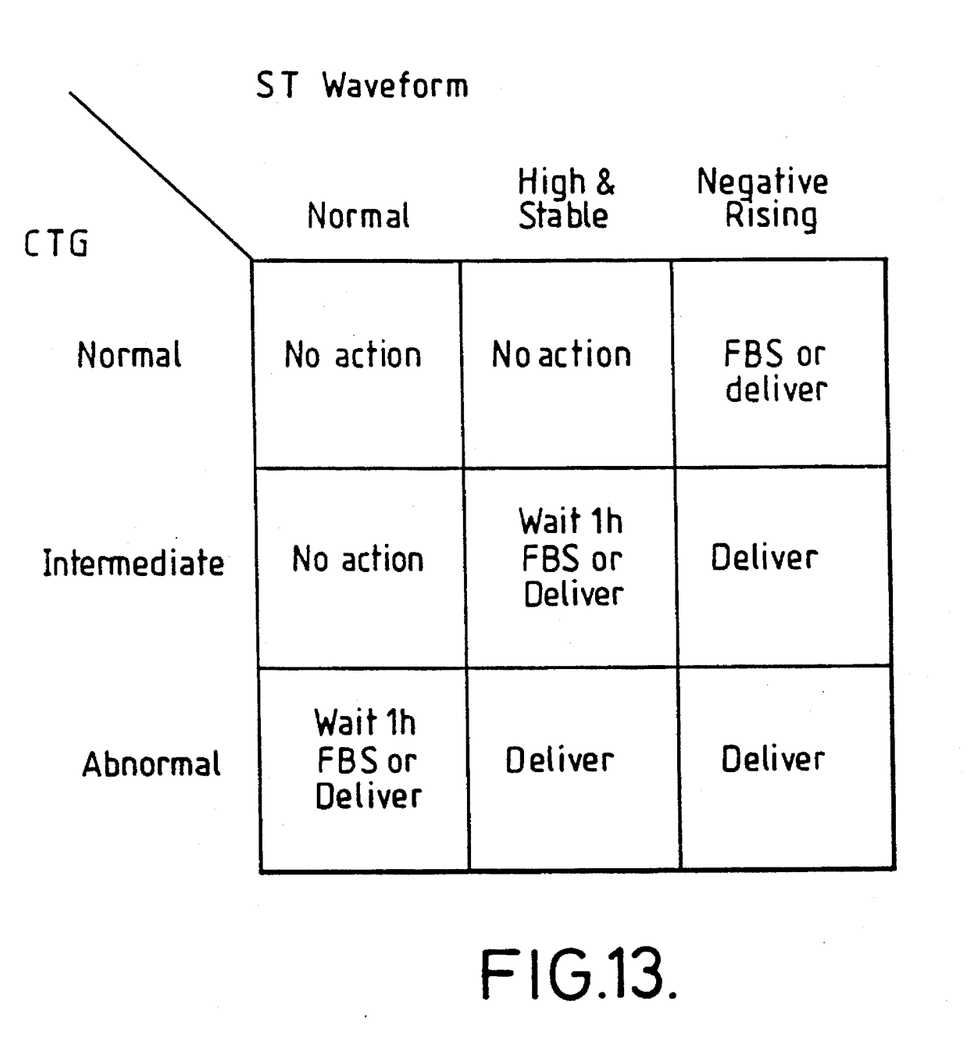
FIG. 13 shows a method of interpreting an ST waveform.

Information relating to progressive changes in the ST waveform in the presence of CTG abnormalities better identify a compromised foetus than the CTG alone. A method for interpreting this information is shown in FIG. 13. This technique is likely to reduce foetal blood sampling and has been shown to reduce unnecessary operative intervention.

It will be understood by the skilled man that the figures given above for thresholds are to be taken as approximate indications only, and that these figures may be varied in order to adjust the operation of the analyser.

We claim:

1. A foetal monitor comprising:

a sensing device including sensors for measuring uterine movement and foetal heart rate, of a patient under observation, a data collection device, coupled to the sensing device and arranged to receive and sample an output signal of the sensing device and to generate digital signals representative of the parameter over a predetermined time interval, data analysis means including recognition means operable periodically to calculate a baseline heart rate value by calculating a plurality of modal values for a respective plurality of modal ranges of the measured foetal heart rate over a predetermined time interval of the foetal heart rate and to recognize in the digital signals received over a signal link from the data collection device a plurality of predetermined information features by automatically analyzing the digital signals in relation to the baseline heart rate value and classification means for classifying at least one of the said features, to produce first output signals representative of the existence of such features and representative of feature classifications, signal storage means arranged to receive and store the said first output signals as a short term knowledge base, database storage means for storing reference data as long term knowledge base, database storage means for storing reference data as a long term knowledge base, an inference engine arranged to process signals representative of the short term and long term knowledge bases automatically to produce conclusion signals, and indication means arranged to receive the conclusion signals and to provide an indication of said conclusion signals.

2. A foetal monitor according to claim 1, further comprising at least one operator entry interface including means for entering patent-specific data to produce second output signals and wherein the signal storage means is coupled to at least one operator entry interface and is arranged to receive and store the first and second output signals as a short term knowledge base.

3. A foetal monitor according to claim 2, wherein the indication provided by the indication means includes a recommendation and/or request for operator entry via at least one operator entry interface.

4. A foetal monitor according to claim 1, wherein the classification means is operable to classify a heart rate deceleration as present or absent and if present, its size, and timing in relation to uterine contractions.

5. A foetal monitor according to claim 1, wherein the data analysis means includes means for generating an adjusted baseline heart rate value which deviates from the normally calculated value when predetermined features of the digital signal are recognized.

6. A foetal monitor according to claim 1, wherein one of the information features is a heart rate deceleration and wherein the recognition means is operable to quantify, for a set of the digital signals representing a foetal heart rate lower than the baseline heart rate, the period of time for which the heart rate is lower than the baseline heart rate, the magnitude of the greatest deviation below the baseline heart rate, the variability of the heart rate, and the area encompassed by a heart rate waveform represented by the set and a waveform representation of the portion of baseline heart rate corresponding to the start and finish of the set.

7. A foetal monitor according to claim 6, wherein a deceleration which has been recognized is classified at least as a normal or severe deceleration and wherein the classification is performed by a neural network.

8. A foetal monitor according to claim 6, wherein the recognition of a heart rate deceleration includes comparing the greatest deviation below the baseline heart rate with a predetermined threshold and in which the threshold is variable according to the variability of the heart rate.

9. A foetal monitor according to claim 1, wherein one of the information features is a heart rate acceleration and wherein the recognition means is operable to quantify for a set of the digital signals representing a foetal heart rate higher than the baseline heart rate, the period of time for which the heart rate is higher than the baseline heart rate, the magnitude of the greatest deviation above the baseline heart rate, and the area encompassed by the heart rate waveform represented by the set and a waveform representation of the portion of baseline heart rate corresponding to the start and finish of the set.

10. A foetal monitor according to claim 1, wherein one of the information features is heart rate variability and wherein the classification means is operable to quantify, for a set of the digital signals representing foetal heart rate, the difference between two predetermined variance levels of a statistical frequency distribution of the set.

11. A foetal monitor according to claim 10, wherein the classification of variability includes selecting the set of digital signals from a portion of the heart rate waveform not having a deceleration or acceleration.

12. A foetal monitor according to claim 1, wherein one of the information features is a uterine contraction, and wherein the recognition means is operable to calculate the statistical frequency distribution of a first set of the digital signals representing uterine movements, to derive a ground level value by finding the value of the uterine movement signal at a predetermined variance level of the statistical frequency distribution and to quantify, for a second set of the digital signals representing a uterine movement signal deviating by more than a predetermined amount from the ground level, at least one of: the period of time for which the movement signal deviates from the ground level, the magnitude of the greatest deviation from the ground level, and the area encompassed by a uterine movement waveform represented by the second set and a waveform representation of the portion of the ground level corresponding to the start and finish of the second set.

13. A foetal monitor according to claim 1, wherein the sensing device includes a sensor for measuring a foetal ECG and wherein the data collection device is arranged to produce a digital signal representative of the ST waveform of a measured ECG, and in which the inference engine is operable to process signals representative at least of foetal heart rate and the ST waveform to produce the conclusion signals.

14. A foetal monitor according to claim 1, wherein the indication means includes an explanation device operable to explain the processing in the inference engine which has led to the current conclusion signals.

* * * * *